United States Patent [19]

Kyo et al.

[11] 4,224,252
[45] Sep. 23, 1980

[54] PRODUCTION OF PINACOLONE

[75] Inventors: Sunao Kyo; Haruo Tsuchiya; Hidetsugu Tanaka, all of Kashima, Japan

[73] Assignee: Kuraray Co., Ltd., Kurashiki, Japan

[21] Appl. No.: 39,300

[22] Filed: May 15, 1979

[51] Int. Cl.² ............................................. C07C 45/02
[52] U.S. Cl. .................................. 568/388; 568/386; 568/391; 568/393; 568/397; 568/405
[58] Field of Search .................... 260/593 R, 594, 597

[56] References Cited

U.S. PATENT DOCUMENTS

| | | | |
|---|---|---|---|
| 4,057,583 | 11/1977 | Merz et al. | 260/593 R |
| 4,059,634 | 11/1977 | Smith | 260/593 R |
| 4,146,581 | 3/1979 | Nissen | 260/593 R |

Primary Examiner—Bernard Helfin
Assistant Examiner—James H. Reamer
Attorney, Agent, or Firm—Barry Kramer

[57] ABSTRACT

Disclosed are improved procedures for preparing pinacolone from compounds of general formula (I)

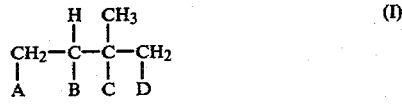

wherein, either adjacent two of A, B, C and D form a single bond between them and the remaining two are hydrogen atoms, or both A and D are hydrogen atoms and one of B and C is a hydrogen atom and the other represents OH, Cl, Br, HSO$_4$, H$_2$PO$_4$ or ClO$_4$, and a new procedure which enables preparing pinacolone from a compound of general formula (II)

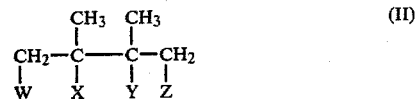

wherein, both W and Y are each hydrogen atoms and X and Z are the same or different and each represents OH, Cl, Br, HSO$_4$, H$_2$PO$_4$, ClO$_4$ or RCOO wherein R is a hydrogen atom or an alkyl group of 1 to 3 carbon atoms, or one of W and Y is a hydrogen atom and the other forms a single bond together with X, and Z represents OH, Cl, Br, HSO$_4$ H$_2$PO$_4$, ClO$_4$ or RCOO where R is defined as above. In the process of preparing pinacolone from compounds of formula (I) by reacting them with formaldehyde in the presence of a strong inorganic acid, the process can be improved by adding a salt of a strong inorganic acid, or a compound of formula (II). Pinacolone can also be produced by heating a compound of general formula (II) in the presence of a strong inorganic acid and this reaction, too, can be improved by the addition of a salt of a strong inorganic acid. The use of a salt of a strong inorganic acid according to the invention makes it possible to reduce the concentration and the amount of strong acid normally required, and to improve the yield of pinacolone.

37 Claims, No Drawings

PRODUCTION OF PINACOLONE

BACKGROUND OF THE INVENTION

1. Field of the Invention

This invention relates to production of pinacolone (or tertiary-butyl methyl ketone).

2. Description of the Prior Art

It is well known in the field of organic chemistry that pinacolone can be produced via pinacol from acetone. The process involves the so-called pinacol-pinacolone rearrangement (cf. e.g. Organic Syntheses, Collective Volume 1, pages 459–463). The process comprises reacting acetone with metallic magnesium (or metallic aluminum) in the presence of mercuric chloride, hydrolyzing the resulting magnesium (or aluminum) salt of pinacol and treating the resulting pinacol with sulfuric acid to cause dehydration and said rearrangement. The case where metallic magnesium is used may be illustrated by the following equations (1)–(3):

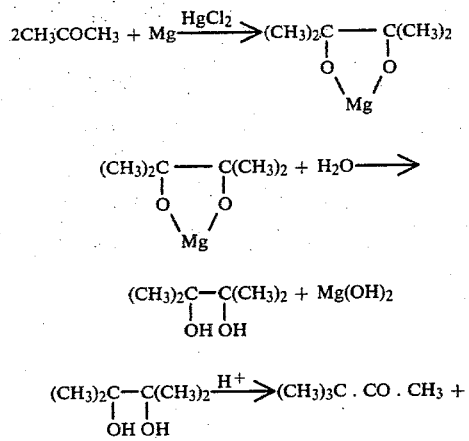

In commercial scale production, however, this method is disadvantageous from economical and socio-environmental standpoints. The reasons, among others, are that: the fairly expensive metallic magnesium or aluminum used as one of the raw materials is converted into a useless salt; toxic mercuric chloride is required, and during the reaction the major part of it is converted into elemental mercury, which is very difficult to be isolated quantitatively from the reaction mixture; and acetone is employed in a large excess, and a part of this is reduced to give a large amount of isopropyl alcohol as a byproduct which necessitates the use of large quantities of energy to recover and purify the excess acetone. Because of potential environmental problems, it would be advantageous to provide a process with reduced use and formation of hazardous substances and reduced formation of industrial wastes.

An alternative method is also known which comprises hydrolyzing in the presence of a strong acid, 4,4,5-trimethyl-1,3-dioxane obtained by Prins reaction of 2-methylbutene-2 with formaldehyde (see German Patent No.714,488, Chemical Abstracts, vol. 78, 71330d (1973) and U.S. Pat. No. 4,059,634). The reactions involved may be illustrated by the following equations (4) and (5):

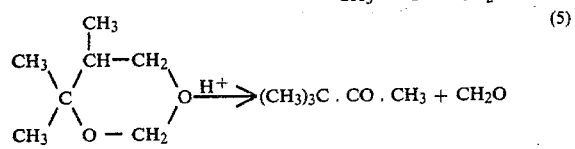

This process, also, has such drawbacks as: the decreased yield of pinacolone; the simultaneous formation of formaldehyde, followed by its consecutive consumption; the formation of a considerable amount of viscous byproduct; and the necessity of recovery or separation of the byproducts from pinacolone, whereby the reaction process becomes complicated and the purity of the product is decreased.

An improved method has been proposed to avoid such disadvantages, which method comprises adding formalin slowly to 2-methylbutene-2 or 2-methylbutene-1 or an acid adduct of either of these butenes in the presence of an inorganic acid to cause formation of pinacolone (cf. U.S. Pat. No. 4,057,583). This method provides pinacolone in increased yield in one reaction step, as compared with the method of the German Patent cited above.

However, the minimum inorganic acid concentration necessary for the reaction is at least as high as 15 weight %, and to obtain satisfactory results, it is necessary to use a large quantity of a highly concentrated acid. In the exemplary case of hydrochloric acid, which is said to give the best results, the minimum concentration applied in the examples of the U.S. Pat. No. 4,057,583 is 30 weight % and the amount required is 2 moles or more per mole of a 2-methylbutene. This means that a large amount of hydrochloric acid needs to be employed in high concentration for obtaining a satisfactory reaction yield and that the resulting pinacolone will be contaminated with a considerable amount of the acid, whereby various disadvantages are caused in purification of pinacolone. Moreover, the necessity of using highly concentrated hydrochloric acid causes various disadvantages in the commercial application of the process. Reuse of the aqueous acid solution is complicated because the acid, which is diluted during the reaction, is very difficult to reconcentrate by conventional distillation to a hydrogen chloride concentration beyond 20.24 weight %. Generally, aqueous hydrochloric acid solution forms an azeotropic mixture with water at this concentration. It is possible to increase the acid concentration by addition of hydrogen chloride, as described in the example of the U.S. Pat. No. 4,057,583; however, this procedure is very disadvantageous because it inevitably increases the total volume of acid.

SUMMARY OF THE INVENTION

It has now been found that the above problems can be solved in a very simple manner in accordance with the present invention which provides improved procedures for producing pinacolone from compounds of general formula (I)

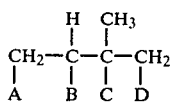

(I)

wherein, either adjacent two of A, B, C and D form a single bond between them and the remaining two are hydrogen atoms, or both A and D are hydrogen atoms and one of B and C is a hydrogen atom and the other represents OH, Cl, Br, $HSO_4$, $H_2PO_4$ or $ClO_4$, and a new procedure which enables preparing pinacolone from a compound of general formula (II)

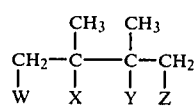

(II)

wherein, both W and Y are each hydrogen atoms and X and Z are the same or different and each represents OH, Cl, Br, $HSO_4$, $H_2PO_4$, $ClO_4$ or RCOO wherein R is a hydrogen atom or an alkyl group of 1 to 3 carbon atoms, or one of W and Y is a hydrogen atom and the other forms a single bond together with X, and Z represents OH, Cl, Br, $HSO_4$, $H_2PO_4$, $ClO_4$ or RCOO where R is defined as above. In the process of preparing pinacolone from compounds of formula (I) by reacting them with formaldehyde in the presence of a strong inorganic acid, the process can be improved by adding a salt of a strong inorganic acid, or a compound of formula (II). Pinacolone can also be produced by heating a compound of formula (II) in the presence of a strong inorganic acid and this reaction, too, can be improved by the addition of a salt of a strong inorganic acid. The use of a salt of a strong inorganic acid according to the invention makes it possible to reduce the concentration and the amount of strong acid normally required, and to improve the yield of pinacolone.

DETAILED DESCRIPTION OF THE INVENTION

The compounds represented by the above general formula (I) which can be used as starting materials in the present invention are: butenes such as 2-methylbutene-1, 2-methylbutene-2 and 3-methylbutene-1; adducts of said butenes with sulfuric phosphoric or perchloric acid; and, butene derivatives, such as 2-methyl-2-chlorobutane, 2-methyl-2-bromobutane, 2-methyl-3-chlorobutane, 2-methyl-3-bromobutane, 2-methylbutan-2-ol and 3-methylbutan-2-ol. These butenes can be obtained easily on a commercial scale by partial hydrogenation of isoprene, for instance. The butene derivatives can be obtained on a commercial scale, for example, by addition of hydrogen chloride, hydrogen bromide, water, sulfuric acid, phosphoric acid, perchloric acid and so on to said 2-methylbutene-1, 2-methylbutene-2 or 3-methylbutene-1.

Compounds of general formula (II) which can be employed are: 2,3-dimethyl-butan-1,3-diol, 2,3-dimethyl-3-chlorobutan-1-ol, 2,3-dimethyl-3-bromobutan-1-ol, 2,3-dimethyl-3-buten-1-ol, 2,3-dimethyl-2-buten-1-ol, esters of these alcohols with sulfuric, phosphoric or perchloric acid or with an aliphatic carboxylic acid containing 1-4 carbon atoms, and the like.

The compound of general formula (II) may be added to the reaction system alone or in admixture with a compound of formula (I), with formaldehyde, or with a compound of general formula (I) and formaldehyde.

In the reaction employing compounds of formula (II), like that employing those of formula (I), the concentration and quantity of the strong inorganic acid can be reduced, without any decrease in yield, by adding a salt of a strong inorganic acid at least partially soluble in the reaction system. In this case, the compound of general formula (II) is heated in an aqueous solution of a strong inorganic acid and a salt of a strong inorganic acid to produce pinacolone. The reactions involved in the cases of 2,3-dimethyl-3-chlorobutan-1-ol acetate and 2,3-dimethyl-2-butene-1-ol as starting materials, respectively, may be represented by the following equations:

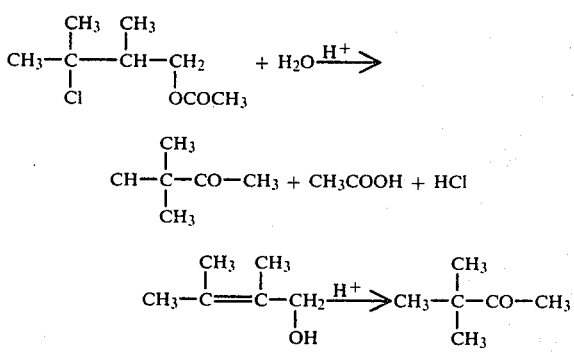

It has been also established that pinacolone can be obtained in increased yield by adding a compound of general formula (II) to the system of reaction of a compound of general formula (I) shown above with formaldehyde.

Formaldehyde may be used in the form of a solution of formaldehyde, a compound capable of yielding formaldehyde under the reaction conditions (hereinafter called "formaldehyde source compound") or a solution thereof. Representative of compounds usable for preparing a formaldehyde solution include, in addition to water, such alcohols as 2-methylbutan-2-ol, 3-methylbutan-2-ol, 2,3-dimethylbutan-1,3-diol, 2,3-dimethyl-3-chlorobutan-1-ol, 2,3-dimethyl-3-bromobutan-1-ol, 2,3-dimethyl-3-buten-1-ol and 2,3-dimethyl-2-buten-1-ol, and esters of these with carboxylic acids containing 1-4 carbon atoms. When these compounds are used, the formaldehyde solutions preferably have concentrations of 3-35 weight %. Formaldehyde may also be used in the form of a solution dissolved in a mixture of these compounds and water.

The formaldehyde source compound is, for example, an acyclic or cyclic formal or hemiformal of 2-methylbutan-2-ol, 3-methylbutan-2-ol, 2,3-dimethylbutan-1,3-diol, 2,3-dimethyl-3-chlorobutan-1-ol, 2,3-dimethyl-3-bromobutan-1-ol, 2,3-dimethyl-3-buten-1-ol or 2,3-dimethyl-2-buten-1-ol, or an ester of such hemiformal with a carboxylic acid containing 1-4 carbon atoms.

One of the advantages attainable by using formaldehyde in the form of a solution in one of the above-mentioned compounds other than water, or in the form of one of the above formaldehyde source compounds, is that the pinacolone yield can be improved without giving any special consideration to the manner of separating reaction productions because the reaction yields formaldehyde and compounds represented by general formula (I), pinacolone intermediates or the objective compound, i.e. pinacolone. A further advantage is that dilution of the aqueous solution of the strong inorganic acid and the salt of strong inorganic acid used for the reaction is eliminated or reduced as compared with the case where an aqueous solution of formaldehyde is employed. From the standpoint of commercial availability, however, formaldehyde is used generally in a form of a 5-70 weight %, preferably 15-55 weight % aqueous solution.

The reaction which occurs when a formaldehyde source compound is used instead of an aqueous formaldehyde solution may be exemplified by the following equation which is concerned with the reaction of 2-methyl-2-butene and the cyclic formal of 2,3-dimethylbutan-1,3-diol (or 4,4,5-trimethyl-1,3-dioxane):

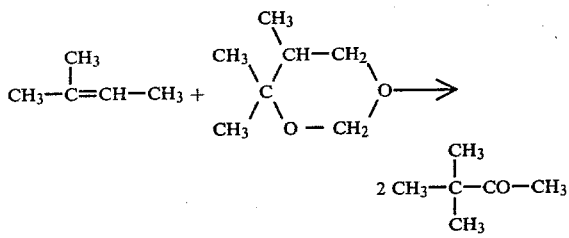

The alcohols and derivatives thereof (carboxylates, formals, hemiformals and carboxylate esters of said hemiformals) represented by general formula (II) above can be prepared easily by reacting 2-methyl-2-butene with formaldehyde, for instance (see, for example, Chemical Reviews, vol. 51, 505 (1952) and Bull. Soc. Chim. France, 4178 (1967)).

Preferably, formaldehyde is used in an amount of 0.5-1.5 moles per mole of the compound of general formula (I). Although an amount of formaldehyde beyond the above range may be employed, it results in no better yield and is uneconomical because of the loss of starting compounds and the deterioration of the quality of pinacolone. It is especially preferred to use 0.8-1.1 moles of formaldehyde per mole of the compound of general formula (I). In cases where formaldehyde is fed wholly or partly in the form of a formaldehyde source compound, the total theoretical amount of formaldehyde which is to be formed from the said compound should also be within the above range.

The preferred strong inorganic acids are hydrochloric, hydrobromic, sulfuric, phosphoric and perchloric acids, alone or in admixture of two or more or these. Especially preferred are hydrochloric and sulfuric acids in view of yield and other respects.

While the acid concentration of the aqueous region in the reaction mixture varies during the reaction due to dilution with the added aqueous formaldehyde solution or with water resulting from the reaction, it is desirable according to the invention that the concentration of the strong inorganic acid in the aqueous region in the reaction mixture is maintained at 0.5 mole/kg or more, preferably at 1.0 mole/kg or more, throughout the whole reaction period and that the amount of the strong inorganic acid in said aqueous region is at least 0.1 mole per mole of formaldehyde used for the reaction. When the starting material is an adduct of a 2-methylbutene and a strong inorganic acid, or when the formaldehyde solution contains a compound which has a radical of a strong inorganic acid, or when the formaldehyde source compound is a formal or hemiformal of a compound which has a radical of a strong inorganic acid, the concentration and amount of said strong inorganic acid are generally maintained at lower levels within said range than those in different cases.

The salt of strong inorganic acid to be used together with the strong inorganic acid is required to be at least partly soluble in the reaction system. It is preferred that the solubility of the salt in water is at least 35 grams per hundred grams of water at 100° C. Acidic salts as well as neutral salts can be used. Examples are chlorides and bromides of lithium, sodium, potassium, rubidium, cesium, copper (II), magnesium, calcium, strontium, barium, zinc, cadmium, aluminum, scandium, zirconium, titanium (IV), tin (IV), manganese (II), iron, cobalt (II), nickel and so on, sulfates of ammonium, sodium, rubidium, cesium, magnesium, cadmium, zinc, aluminum, cobalt (II), copper (II), nickel (II), manganese (II) and so on, perchlorates of lithium, calcium, silver, strontium, sodium, barium, magnesium and so on, acidic salts such as sodium hydrogen sulfate, potassium hydrogen sulfate, ammonium dihydrogen phosphate, sodium dihydrogen phosphate and so on, and further, double salts such as magnesium potassium chloride sulfate, and so on. Among these, those that have a relatively high molar solubility and a high stability in the aqueous phase under the reaction conditions are suitable. From this point of view together with economic availability, alkali and alkaline earth metal salts of hydrochloric or sulfuric acid, especially sodium chloride, potassium chloride, lithium chloride, calcium chloride, magnesium chloride, sodium hydrogen sulfate, potassium hydrogen sulfate, lithium hydrogen sulfate and magnesium sulfate, are preferred. The acid radical of the strong inorganic acid and that of the salt of strong inorganic acid need not be always the same, but such combinations as would cause the formation of relatively insoluble salts under the reaction conditions should be avoided. Similarly, while two or more strong inorganic acid salts may be used in admixture, those combinations which would form difficultly soluble salts under the reaction conditions should be avoided.

The amount of the salt of strong inorganic acid is controlled, depending upon the concentration of the strong inorganic acid in the aqueous phase under the reaction conditions, so that it may be small when the concentration of the strong inorganic acid is high and, conversely, large when the concentration of the strong inorganic acid is high and, conversely, large when the concentration of said strong inorganic acid is low. It is desirable to maintain the total amount of the acid radical of the salt of strong inorganic acid plus the acid radical of the strong inorganic acid in the range of 3.0-9.0 moles per kilogram of the aqueous phase in the reaction system.

Particularly in accordance with the present invention, high yields of pinacolone can be achieved by using a solution of strong inorganic acid salts dissolved in an aqueous strong inorganic acid having concentration of 3-13 weight %, provided that the amount of the said acid is 0.5-1.5 moles per mole of formaldehyde to be added during the reaction and that the total concentration of both acid radicals from the acid and the acid salt is adjusted in a range of 5.0-8.0 moles per kilogram of the aqueous region in the reaction mixture.

As mentioned previously, when an acid radical of a strong inorganic acid is contained in the starting material represented by general formula (I) and in the formaldehyde source compound, or when the formaldehyde solution contains a compound having an acid radical of a strong inorganic acid, high yields of pinacolone can be obtained with a still lower concentration and still smaller amount of the strong inorganic acid. This means that, by using a salt of a strong inorganic acid, the reaction can be carried out in good yields at far lower concentrations and much smaller amounts of the strong inorganic acid than required in the known methods. Therefore, the present invention has a very profound industrial significance along with the additional advantages in respect to the simplified isolation and purification of the product, re-use of the strong inorganic acid, and cost or maintenance of the apparatuses, etc.

The reaction may also be carried out in the presence of an inert diluent other than water. Examples of suitable diluents are hydrophobic compounds such as saturated hydrocarbons, chlorinated hydrocarbons and ketones, e.g. methylbutane, hexane, cyclohexane, butyl chloride, 1,1,1-trichloroethane, 1,1,1,2-tetrachloroethane, carbon tetrachloride and pinacolone. However, no special advantage can be obtained by the use of such diluent.

The reaction is preferably carried out at a temperature within the range of 40°–200° C., especially 70°–150° C. It is preferred to heat the reaction mixture to a temperature of at least 80° C. at the late stage of reaction so that it goes essentially to a satisfactory extent. The reaction is continued for a time effective to complete it to a satisfactory extent. The reaction is carried out at atmospheric pressure or above, generally at a pressure between atmospheric pressure and 30 kg/cm². When the reaction is effected at a temperature equal to or higher than the boiling point of the reaction mixture, an autogenous pressure resulting from said reaction mixture at the reaction temperature is suitable as reaction pressure. There is no special necessity of increase the pressure with an inert gas.

The procedure for carrying out the reaction may be any of: (1) the procedure comprising adding a compound of general formula (I) and formaldehyde and/or a formaldehyde source compound continuously or portionwise to an aqueous solution containing a strong inorganic acid plus a strong inorganic acid salt maintained at a given reaction temperature with stirring; (2) the procedure comprising adding formaldehyde and/or a formaldehyde source compound slowly to an aqueous solution containing a compound of general formula (I), a strong inorganic acid and a strong inorganic acid salt being stirred vigorously at a given reaction temperature; or (3) the procedure comprising mixing an aqueous solution containing a compound of general formula (I), a strong inorganic acid, and a strong inorganic acid salt, with formaldehyde and/or a formaldehyde source compound, and maintaining the resulting mixture under vigorous agitation and at reaction conditions such as temperature and the like to effect the reaction. In view of yields of the reaction, procedures (1) and (2) are preferable, and especially procedure (1) is preferred. The process according to the present invention can be conducted either continuously or batchwise. Since the reaction mixture forms a heterogeneous system, vigorous stirring is necessary in effecting the reaction. The reaction can also be carried out in the presence of a surface active agent. Naturally, the reaction period required varies depending upon such factors as quantity of each starting material, concentration and amount each of the strong inorganic acid and the strong inorganic acid salt in the aqueous solution, the reaction temperature, and the reaction procedure, but generally it is 1–20 hours.

After completion of the reaction, pinacolone can be isolated from the reaction mixture by: (a) separation of the organic layer from the aqueous phase followed by distillation of said organic layer, if necessary after neutralization thereof; (b) neutralization of the reaction mixture followed by distillation of said mixture or the organic layer alone; or (c) distillation of the reaction mixture as it is, or by some other method. With methods (a) and (c), it is possible to recycle the whole or a part of the aqueous layer containing a strong inorganic acid and an acid salt to the reaction system. In view of efficient isolation or recovery of pinacolone, method (a) is preferred. Steam distillation and/or usual distillation under a reduced or atmospheric pressure may be employed as method of distillation.

The use of strong inorganic acid salts in the process according to the present invention reduces the partition of organic components to the aqueous region and the partition of the strong inorganic acid to the organic region when the reaction mixture is separated into the organic and aqueous phases. This makes it advantageous to recycle the whole or a part of the aqueous phase to the reaction system, directly after separation from the organic region or after concentration where necessary. This also enables the isolation and recovery of highly pure pinacolone in good yields. Those low-boiling components that are obtained on distilling the organic layer of the reaction mixture are mainly 2-methylbutenes, 2,3-dimethylbutadiene and other starting materials or pinacolone precursors, and accordingly, can be recycled in the form of a mixture as is.

Pinocolone, the product of the process of the present invention, is a commercially important solvent and as an intermediate for the syntheses of agricultural chemicals and rubber chemicals.

The present invention will be better understood by reference to the following examples, which are meant to illustrate the present invention while not limiting it in any way. The yields mentioned in the examples mean, unless otherwise stated, mol percent based on the sum of the amount of formaldehyde fed to the reaction system and the theoretical amount of formaldehyde to be formed from the formaldehyde source compound fed to the reaction system.

EXAMPLES 1–4

A 500-ml four-necked flask equipped with stirrer, reflux condenser, thermometer and inlet for feeding starting materials, which inlet was connected with a micrometering pump, was charged with hydrochloric acid having a concentration as specified in Table 1 and calcium chloride of such an amount that a concentration as specified in Table 1 might be obtained, and a mixture of 39.6 g (0.45 mole) of 2-methylbutan-2-ol and 45 g of 30% formalin (0.45 mole of formaldehyde) was introduced over 6 hours while heating the contents at 98° C. with stirring. After completion of the introduction, refluxing was continued for further 3 hours, to complete the reaction. The reaction mixture was cooled on an ice water bath and an equivalent amount of sodium hydroxide was added with stirring to cause neutralization. After the neutralization, the mixture was allowed to separate into two layers. The lower layer (aqueous phase) was analyzed for formaldehyde content by the sodium sulfite method. In each case, almost no formaldehyde was detected. The upper layer (organic region) was analyzed by gas chromatography. The results are shown in Table 1. In the table, the "temperature at the end of the reaction" means the temperature of the reaction mixture as recorded when the reaction was stopped.

Table 1

| Example | 1 | 2 | 3 | 4 |
|---|---|---|---|---|
| Reaction conditions | | | | |
| Hydrochloric acid concentration[1] (weight %) | 10 | 10 | 7.5 | 5 |
| Hydrochloric acid amount (molar ratio HCl/HCHO) | 1.0 | 1.0 | 1.0 | 1.0 |
| Calcium chloride concentration[2] (weight %) | 23.3 | 18.6 | 18.6 | 25.3 |
| Chloride ion concentration[3] | 6.30 | 5.58 | 5.02 | 5.59 |
| Temperature at the end of the reaction (°C.) | 85.0 | 84.0 | 85.8 | 86.5 |
| Products | | | | |
| Pinacolone (% yield) | 71.5 | 69.8 | 68.2 | 72.5 |
| 2-Methylbutenes (% yield) | 3.5 | 3.4 | 3.7 | 3.0 |
| 2,3-Dimethylbutadiene (% yield) | 0.4 | 0.9 | 1.1 | 0.7 |
| 2-Methyl-2-chlorobutane (% yield) | 3.8 | 2.2 | 0.9 | 1.5 |

Notes:
[1]Concentration of the hydrochloric acid fed to the reaction system.
[2]Concentration of calcium chloride in the aqueous solution resulting from dissolution of calcium chloride in said hydrochloric acid.
[3]Number of moles of chloride ion per kilogram of the aqueous region on the supposition that the hydrochloric acid and calcium chloride used are wholly dissociated in the aqueous solution.

The same shall apply hereinafter.

EXAMPLES FOR COMPARISON 1-2

The procedure of Example 1 was followed except that 10 or 20 weight % hydrochloric acid was used either without the addition of calcium chloride or with the addition of calcium chloride in an excessively large amount. The results were as shown in Table 2.

Table 2

| Example for Comparison | 1 | 2 |
|---|---|---|
| Reaction conditions | | |
| Hydrochloric acid concentration (weight %) | 10 | 20 |
| Hydrochloric acid amount (molar ratio HCl/HCHO) | 1.0 | 1.1 |
| Calcium chloride concentration (weight %) | 0 | 35.6 |
| Chloride ion concentration | 2.74 | 9.95 |
| Temperature at the end of the reaction (°C.) | 74.0 | 75.6 |
| Results of the reaction | | |
| Conversion of formaldehyde (%) | 100 | 100 |
| Pinacolone yield (%) | 27.5 | 36.2 |

EXAMPLES 5-9

The procedure of Example 1 was followed except that the chloride salts shown in Table 3 were used as salts of strong inorganic acid to be added to the reaction system and each reaction mixture was treated and analyzed similarly. The results obtained are shown in Table 3. No remaining formaldehyde was detected in any of the aqueous region after the reaction.

Table 3

| Example | 5 | 6 | 7 | 8 | 9 |
|---|---|---|---|---|---|
| Reaction conditions | | | | | |
| Kind of salt of strong inorganic acid | LiCl | MgCl$_2$ | AlCl$_3$ | TiCl$_4$ | CuCl$_2$ |
| Salt concentration (weight %) | 17.1 | 19.5 | 18.0 | 19.4 | 29.3 |
| Chloride ion concentration | 6.29 | 6.24 | 6.29 | 6.28 | 6.31 |
| Yield of products (%) | | | | | |
| Pinacolone | 71.7 | 71.0 | 66.8 | 75.8 | 60.2 |
| 2-Methylbutenes | 3.8 | 3.1 | 2.9 | 1.1 | 1.2 |
| 2,3-Dimethylbutadiene | 0.3 | 0.2 | 0.3 | 0 | 0 |

Table 3-continued

| Example | 5 | 6 | 7 | 8 | 9 |
|---|---|---|---|---|---|
| 2-Methyl-2-chlorobutane | 2.2 | 3.4 | 1.2 | 0.1 | 0.1 |

Notes:
Concentration of the hydrochloric acid fed was 10 weight %; HCl/2-Methylbutan-2-ol/HCHO = 1/1/1 (molar ratio).

EXAMPLE 10

A one-liter reaction vessel similar to the four-necked flask used in Example 1 was charged with 450 g of aqueous 0.37 weight % hydrochloric acid, and 150 g of calcium chloride was added thereto and dissolved therein with heating and stirring. When the temperature of the aqueous solution reached 98° C., simultaneous introduction of 47.9 g (0.45 mole) of 2-methyl-2-chlorobutane and 45 g of 30 weight % formalin was started through different inlets by means of micrometering pumps, the introduction being carried out over 6 hours. After completion of the introduction of said starting materials, the reaction mixture was further stirred at the refluxing temperature. The reaction mixture was treated and analyzed as in Example 1. Table 5 shows the results together with the results obtained without the addition of calcium chloride (Example for Comparison 3). After these reactions, no formaldehyde remained in the aqueous region of the reaction mixture.

Table 4

| | Example 10 | Example for Comparison 3 |
|---|---|---|
| Reaction conditions | | |
| Hydrochloric acid concentration (weight %) | 0.37 | 0.37 |
| Hydrochloric acid amount (molar ratio HCl/starting material) | 0.10 | 0.10 |
| Calcium chloride concentration (weight %) | 34.6 | 0 |
| Chloride ion concentration | 6.30 | 0.1 |
| Products | | |
| Pinacolone (% yield) | 58.0 | 2.5 |
| 2-Methylbutenes (% yield) | 3.5 | 2.3 |
| 2,3-Dimethylbutadiene (% yield) | 0 | 6.1 |
| 4,4,5-Trimethyl-1,3-dioxane (% yield) | 0 | 12.8 |
| Unreacted 2-methyl-2-chlorobutane (%) | 3.7 | 0 |

EXAMPLE 11

Using the same apparatus as that used in Example 10, the procedure of Example 1 was followed except that 1.0 mole of 3-methylbutan-2-ol was used in place of 0.45 mole of 2-methylbutan-2-ol, with the remaining compositions and reaction conditions unchanged. The temperature of the reaction mixture at the end of the reaction was 86.2° C. Similar treatment and analysis as in Example 1 gave the following results:

| | |
|---|---|
| Conversion of formaldehyde | 100% |
| Conversion of 3-methylbutan-2-ol | 88.2% |
| Selectivity toward pinacolone (based on 3-methylbutan-2-ol) | 61.3% |

EXAMPLE 12

A one-liter flask fitted with stirrer, reflux condenser cooled with ice cooled circulating water, thermometer and inlet for feeding formalin (connected to a micrometering pump) was charged with 548 g (1.5 moles) of aqueous 10 weight % hydrochloric acid and 167 g of calcium chloride, thereafter 70 g (1.0 mole) of 2-methylbutenes (96.8% 2-methylbutene-2 and 3.2% 2-methylbutene-1) was added, and then the temperature was raised with vigorous stirring. When the temperature of the mixture reached 41° C., introduction of aqueous 30 weight % formalin was started, and 100 g (1.0 mole) of said formalin was added over 5 hours. At the end of the addition, the temperature of the liquid mixture was 85.8° C. The mixture was then refluxed for 2 hours with stirring. The liquid temperature thus reached 89.9° C. The reaction mixture was treated and analyzed in the same manner as in Example 1. The results are shown in Table 5.

EXAMPLE FOR COMPARISION 4

The procedure of Example 12 was followed except that the addition of calcium chloride was omitted. The temperature at the end of the reaction was 69.5° C. The reaction mixture was treated and analyzed as in Example 12. The results are shown in Table 5.

EXAMPLE FOR COMPARISION 5

The reaction was carried out in the same manner as in Example for Comparison 4 except that 730 g (3.0 moles) of aqueous 15 weight % hydrochloric acid was used and the introduction of aqueous formalin was introduced over 6 hours and the subsequent refluxing for 3 hours. The temperature of the reaction mixture at the end of the reaction was 90.8° C. The reaction mixture was treated and analyzed as in Example 12. The results are shown also in Table 5.

REFERENCE EXAMPLE 1

The reaction was conducted in the same manner as in Example for Comparison 4 except that 365 g (3.0 moles) of 30 weight % hydrochloric acid was used instead of 548 g (1.5 moles) of 10 weight % hydrochloric acid. This reaction corresponds to Example 2 of the previously mentioned U.S. Pat. No. 4,057,583. The results are shown in Table 5.

Table 5

| Example | 12 | Comparison 4 | Comparison 5 | Ref. 1 |
|---|---|---|---|---|
| Reaction conditions | | | | |
| Hydrochloric acid concentration (weight %) | 10 | 10 | 15 | 30 |
| HCl/HCHO (molar ratio) | 1.5 | 1.5 | 3.0 | 3.0 |

Table 5-continued

| Example | 12 | Comparison 4 | Comparison 5 | Ref. 1 |
|---|---|---|---|---|
| Concentration of calcium chloride (weight %) | 23.3 | 0 | 0 | 0 |
| Chloride ion concentration | 6.30 | 2.74 | 4.11 | 8.22 |
| Products (% yield) | | | | |
| Pinacolone | 68.4 | 8.4 | 48.6 | 70.2 |
| 2,3-Dimethylbutadiene | 0.1 | 19.0 | — | 0 |
| 2-Methyl-2-chlorobutane | 1.5 | 0.3 | — | 0.1 |
| 3-Methyl-2-chlorobutane | 0.1 | 0 | — | 0.2 |
| Unreacted methylbutenes (%) | 0.9 | 6.0 | — | 0.1 |

EXAMPLE 13

A 300-ml glass autoclave provided with a magnetic stirrer was charged with 147 g of aqueous 10 weight % sulfuric acid solution (0.15 mole of sulfuric acid) and 38.8 g of magnesium chloride, and the contents were heated with stirring. After the temperature of the aqueous solution reached 100° C., a mixture of 15 g (0.15 mole) of aqueous 30 weight % formalin and 13.2 g (0.15 mole) of 2-methylbutan-2-ol was fed by means of a micrometering pump over 6 hours. After completion of the feeding of said starting materials, stirring was continued for 3 hours at the same temperature. During the reaction, the reaction system was maintained under an autogenous pressure, the maximum pressure being 1.2 kg/cm² (gauge). The reaction mixture was then cooled to room temperature, transferred together with 50 ml of xylene to a separatory funnel. The organic layer was washed with 20 ml of aqueous 3 weight % sodium carbonate solution, then washed with two 20 ml portions of saturated aqueous sodium chloride solution and analyzed by gas chromatography. The results are shown in Table 6.

EXAMPLE 14-15

Using the same reaction apparatus as that used in Example 13, the procedure of Example 13 was followed except that sodium hydrogen sulfate was used instead of magnesium chloride and the aqueous sulfuric acid solution had a concentration of 10 or 20 weight %. The analysis gave the results as shown in Table 6.

EXAMPLE FOR COMPARISON 6

The procedure of Example 13 was followed except that aqueous 30 weight % sulfuric acid solution was used and the addition of magnesium chloride was omitted. The results are also shown in Table 6.

Table 6

| Example | 13 | 14 | 15 | Comparison 6 |
|---|---|---|---|---|
| Reaction conditions | | | | |
| Sulfuric acid concentration & amount (molar ratio H₂SO₄/HCHO) | 10% 1.0 | 10% 1.0 | 20% 1.0 | 30% 1.22 |
| Added salts & their concentration (weight %) | MgCl₂ 20.9 | NAHSO₄ 39.3 | NAHSO₄ 39.3 | 0 |
| Acid anion concentration[1] (moles/kg aqueous phase) | 6.30 | 3.89 | 4.51 | 3.06 |
| Maximum pressure during reaction (kg/cm² gage) | 1.20 | 1.25 | 1.25 | 1.20 |
| Yields of products (mol %) | | | | |
| Pinacolone | 74.9 | 61.4 | 65.9 | 39.5 |
| 2-Methylbutenes | 3.8 | 7.0 | 5.0 | — |
| 2,3-Dimethylbutadiene | 0 | 0.7 | 0.2 | — |
| 2-Methyl-2-chlorobutane | 2.0 | 0 | 0 | — |

Table 6-continued

| Example | 13 | 14 | 15 | Comparison 6 |
|---|---|---|---|---|
| Unreacted 2-methylbutan-2-ol | 2.6 | 4.1 | 4.1 | — |

Note:
[1]The total amount of the acid radical of the strong inorganic acid and the acid radical of the salt of strong inorganic acid in each kilogram of the aqueous solution of these at the beginning of the reaction.

EXAMPLE 16

A 300-ml glass autoclave provided with a magnetic stirrer was charged with 18.5 g of 91.9% pure 4,4,5-trimethyl-1,3-dioxane (cyclic formal of 2,3-dimethylbutan-1,3-diol) as a formaldehyde source compound, which contained 7.8 weight % 4-methyl-4-ethyl-1,3-dioxane, 213.7 g (0.16 mole) of 2-methylbutan-2-ol, 52.0 g (0.14 mole) of aqueous 10 weight % hydrochloric acid and 10.7 g of lithium chloride. The contents were maintained at 100° C. for 6 hours with vigorous stirring. After the reaction, the mixture was cooled on an ice water bath, 70 ml of xylene was then added, the resulting mixture was stirred again, and the organic layer was separated in a separatory funnel. The organic layer was washed once with 30 ml of aqueous 10% sodium carbonate solution and twice with 30 ml of water and analyzed by gas chromatography. It was revealed that the pinacolone yield was 112.3 mol % based on the 4,4,5-trimethyl-1,3-dioxane used.

EXAMPLE 17

The same apparatus as that in Example 16 was charged with 52.0 g (0.14 mole) of aqueous 10% hydrochloric acid and 10.7 g of lithium chloride. The contents were maintained at 100° C. with stirring. Thereto was added a mixture of 18.5 g of the same formaldehyde source compound as used in Example 16 and 13.7 g (0.16 mole) of 2-methylbutan-2-ol by means of a micrometering pump over 4 hours. After completion of the addition, stirring was continued for further 2 hours at the same temperature and then treated and analyzed in the same manner as in Example 16. The pinacolone yield was 146.4 mol % based on the 4,4,5-trimethyl-1,1,3-dioxane charged.

EXAMPLE FOR COMPARISON 7

The procedure of Example 16 was followed except that 100 g (0.77 mole) of aqueous 28% hydrochloric acid was used in place of 52.0 g of aqueous 10% hydrochloric acid and the addition of lithium chloride was omitted. The analysis revealed that the pinacolone yield was 87.1 mol % based on the 4,4,5-trimethyl-1,3-dioxane charged.

EXAMPLE 18

The same reaction apparatus as that used in Example 16 was charged with 80.3 g (0.11 mole) of aqueous 5 weight % hydrochloric acid and 43.2 g of magnesium chloride and the contents were heated to 100° C. with stirring. Then, under this condition, thereto was fed a mixture of 14.3 g (0.11 mole) of 4,4,5-trimethyl-1,1,3-dioxane (composition: 98.06% 4,4,5-trimethyl-1,3-dioxane and 1.55% 4-methyl-4-ethyl-1,3-dioxane and 10.5 g (0.12 mole) of 2-methylbutan-2-ol by means of a micrometering pump over 4 hours. The same condition was maintained for an additional 2 hours with stirring and thereafter the reaction mixture was treated and analyzed in the same manner as in Example 16, giving the following results:

| Pinacolone yield | 130.1% |
|---|---|
| 2,3-Dimethylbutadiene yield | 0.9% |

Each value is expressed as mol % based on the 4,4,5-trimethyl-1, 3-dioxane charged.

EXAMPLE 19

The procedure of Example 18 was followed except that 108 g (C.11 mole) of 10 weight % sulfuric acid and 71.9 g of sodium hyrdrogen sulfate were used instead of the hydrochloric acid and magnesium chloride, respectively. The analysis gave the following results:

| Pinacolone yield | 102.2% |
|---|---|
| 2,3-Dimethylbutadiene yield | 5.5% |

Each value means mol % based on the 4,4,5-trimethyl-1,3-dioxane charged.

EXAMPLE 20

A one-liter four-necked flask equipped with stirrer, reflux condenser, thermometer and starting material feeding inlet connected with a micrometering pump was charged with 274 g (0.75 mole) of aqueous 10 weight % hydrochloric acid and 56.5 g of lithium chloride, and the contents were heated with stirring. After the temperature reached 100° C., a mixture of 27.0 g of aqueous 50 weight % formaldehyde solution and 80.1 g of a mixed alcohol consisting of 49.4 weight % 2-methylbutan-2-ol, 34.0 weight % 2,3-dimethylbutan-1,3-diol and 16.6 weight % 3-methylpentane-1,3-diol was introduced into the above mixture via a micrometering pump over 6 hours. The reaction mixture was kept in a state of refluxing throughout the introduction and for an additional 2 hours. At the end of the refluxing, the reaction mixture showed a temperature of 87.5° C. The reaction mixture was slowly neutralyzed on an ice water bath with sodium hydroxide under vigorous aggitation.

The organic layer was separated and analyzed by gas chromatography for pinacolone content, and the aqueous phase was filtered to remove the salt precipitate and the filtrate analyzed by the sodium sulfite method for formaldehyde. The Pinacolone yield based on the formaldehyde used for the reaction was thus calculated as follows:

| Conversion of formaldehyde | 100% |
|---|---|
| Pinacolone yield | 114.9% (80.3%) |

The value in the parentheses is the pinacolone yield based on the total amount of 2-methylbutan-2-ol and 2,3-dimethylbutan-1,3 diol fed for the reaction.

EXAMPLE FOR COMPARISON 8

The procedure of Example 20 was followed except that the addition of lithium chloride was omitted. The analysis revealed that unreacted formaldehyde did not remain and that the pinacolone yield was 34.5%.

EXAMPLES 21–24

The procedure of Example 20 was followed using aqueous 50 weight % formaldehyde solution together with starting materials, acids, and acid salts specified in Table 7. The analyses gave the results as shown in Table 7. In each case, the conversion of formaldehyde was 100%.

EXAMPLE 25

In the same manner as described in Example 13, the reaction was carried out employing the starting material, sulfuric acid, and sodium hydrogen sulfate as a salt specified in Table 7. The results are shown in Table 7.

EXAMPLES 26–30

A 300-ml four-necked flask equipped with stirrer, reflux condenser, thermometer and dropping funnel was charged with hydrochloric acid and acid salts of the concentration and amounts specified in Table 8, and the contents were heated with stirring. After the temperature reached 100° C., 0.31 mole of 2,3-dimethylbutan-1,3-diol or a derivative thereof shown in Table 8 was added from the dropping funnel over 4 hours. As the starting material is introduced, the reaction mixture began to reflux. After completion of the addition, the mixture was refluxed for additional 2 hours. The temperature at the end of the reaction given in Table 8 means the temperature at which refluxing was stopped. The reaction mixture was treated and analyzed in the same manner as described in Example 20. The results are shown in Table 8. In all the examples, unreacted starting materials were not detected.

EXAMPLE FOR COMPARISON 9

The procedure of Example 26 was followed except that the addition of lithium chloride was omitted. The results are shown in Table 8. No starting material remained at all in the mixture after the reaction.

Table 7

| Example | Composition of starting material | Strong inorg. acid & concentration | Acid/starting material/HCHO (molar ratio) | Salt of strong inorganic acid & concentration | Pinacolone yield* (%) |
|---|---|---|---|---|---|
| 21 | 0.5 mole 2-methylbutan-2-ol<br>0.1 mole 2,3-dimethyl-3-hydroxybutyl acetate | 10% HCl | 1/1/1 | LiCl 17.1% | 88.6 (77.0) |
| 22 | 0.5 mole 2-methylbutan-2-ol<br>0.013 mole 2,3-dimethyl-3-hydroxybutyl acetate<br>0.087 mole 2,3-dimethylbutan-1,3-diol diacetate | 10% HCl | 1/1/1 | LiCl 17.1% | 88.8 (77.2) |
| 23 | 0.5 mole 2-methyl-2-chlorobutane<br>0.1 mole 2,3-dimethyl-3-chlorobutan-1-ol | 3% HCl | 1.1/1/1 | $MgCl_2$ 19.5% | 88.2 (76.1) |
| 24 | 0.5 mole 2-methylbutan-2-ol<br>0.1 mole 2,3-dimethyl-2-buten-1-ol acetate | 10% HCl | 1.1/1/1 | $MgCl_2$ 19.5% | 88.4 (76.5) |
| 25 | 0.15 mole 2-methylbutan-2-ol<br>0.05 mole 2,3-dimethylbutan-1,3-diol | 10% $H_2SO_4$ | 1/1/1 | $NaHSO_4$ 39.3% | 86.4 (67.1) |

*Yield based on the formaldehyde used for the reaction. The values in the parentheses are the yields based on the total amount of the compound of general formula (I) and the compound of general formula (II).

Table 8

| Example No. | 26 | 27 | 28 | 29 | 30 | Comparison 9 |
|---|---|---|---|---|---|---|
| Starting material | 2,3-dimethyl-butan-1,3-diol[1] | 2,3-dimethyl-3-chlorobutyl acetate | 2,3-dimethyl-3-hydroxybutyl acetate | 2,3-dimethyl-2-buten-1-ol acetate | 2,3-dimethyl-butan-1,3-diol diacetate[2] | 2,3-dimethyl-butan-1,3-diol[1] |
| Reaction conditions | | | | | | |
| Hydrochloric acid concentration (weight %) | 10 | 3.0 | 10 | 10 | 10 | 10 |
| HCl/starting material (molar ratio) | 0.97 | 1.5 | 1.5 | 1.5 | 1.99 | 0.97 |
| Salt added and concentration (weight %) | LiCl 17.1 | $MgCl_2$ 20.0 | LiCl 17.1 | $MgCl_2$ 20.0 | LiCl 17.1 | — |
| Chloride ion concentration (moles/kg) | 6.29 | 4.86 | 6.29 | 6.39 | 6.29 | 2.74 |
| Temperature at the end of the reaction (°C.) | 90.5 | 90.5 | 92.0 | 90.2 | 94.0 | 76.0 |
| Pinacolone yield (%) | 83.6 | 84.6 | 85.5 | 83.3 | 86.4 | 44.7 |

Notes:
[1] It contains 9.8% of 3-methylpentan-1,3-diol as an impurity other than the compound of the general formula (II).
[2] It is employed in a form of a mixture including 13.3 mol % of 2,3-dimethyl-3-hydroxybutyl acetone.

What is claimed is:

1. A process for producing pinacolone comprising reacting a compound of the general formula (I)

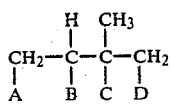

wherein either any adjacent two of A, B, C and D form a single bond between them and the remaining two are hydrogen atoms, or both A and D are hydrogen atoms and one of B and C is a hydrogen atom and the other is OH, Cl, Br, $HSO_4$, $H_2PO_4$ or $ClO_4$, with formaldehyde in the presence of an aqueous solution of an inorganic acid selected from the group consisting of hydrochloric acid, hydrobromic acid, sulfuric acid, phosphoric acid and perchloric acid, and a salt of one or more of said inorganic acids having a solubility of at least 35 grams per hundred grams of water at 100° C.

2. A process according to claim 1, wherein a compound of general formula (I) and formaldehyde are added slowly to an aqueous soltuion containing said inorganic acid and said inorganic acid salt.

3. A process according to claim 1, wherein a compound of the general formula (II)

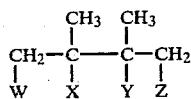

wherein either both W and Y are hydrogen atoms and X and Z are the same or different and each represents OH, Cl, Br, $HSO_4$, $H_2PO_4$, $ClO_4$ or RCOO in which R is a hydrogen atom or an alkyl group of 1 to 3 carbon atoms, or one of W and Y is a hydrogen atom and the other forms a single bond together with X, and Z represents OH, Cl, Br, $HSO_4$, $H_2PO_4$, $ClO_4$ or RCOO, is added to the reaction system.

4. A process according to claim 3, wherein a mixture of a compound of general formula (I) and a compound of general formula (II) is added to the reaction system.

5. A process according to claim 3, wherein a mixture of a compound of general formula (II) and formaldehyde is added to the reaction system.

6. A process according to claim 1, wherein formaldehyde is used in the form of a solution of formaldehyde, a compound capable of yielding formaldehyde under the reaction conditions, or a solution thereof.

7. A process according to claim 6, wherein there is used an aqueous solution of formaldehyde with a concentration of 5-70 weight percent.

8. A process according to claim 7, wherein the solution of formaldehyde has a concentration of 15-55 weight percent.

9. A process according to claim 6 wherein there is used a 3-35 weight percent solution of formaldehyde in an alcohol selected from the group consisting of 2-methylbutan-2-ol, 3-methylbutan-2-ol, 2,3-dimethylbutan-1,3-diol, 2,3-dimethyl-3-chlorobutan-1-ol, 2,3-dimethyl-3-bromobutan-1-ol, 2,3-dimethyl-3-buten-1-ol and 2,3-dimethyl-2-buten-1-ol, or an ester of said alcohol with a carboxylic acid containing 1-4 carbon atoms.

10. A process according to claim 9, wherein the solution of formaldehyde is mixed with water.

11. A process according to claim 6, wherein there is used a compound capable of yielding of formaldehyde under the reaction conditions, said compound being an acyclic or cyclic formal or hemiformal of 2-methylbutan-2-ol, 3-methylbutan-2-ol, 2,3-dimethylbutan-1,3-diol, 2,3-dimethyl-3-chlorobutan-1-ol, 2,3-dimethyl-3-bromobutan-1-ol, 2,3-dimethyl-3-buten-1ol or 2,3-dimethyl-2-buten-1-ol, or an ester of any of said hemiformals with a carboxylic acid containing 1-4 carbon atoms.

12. A process according to claim 1, wherein the salt is an alkali or alkaline earth metal salt of hydrochloric or sulfuric acid.

13. A process according to claim 12, wherein the salt is sodium chloride, potassium chloride, lithium chloride, calcium chloride, magnesium chloride, sodium hydrogen sulfate, potassium hydrogen sulfate, lithium hydrogen sulfate or magnesium sulfate.

14. A process according to claim 1, wherein said inorganic acid is hydrochloric, sulfuric, phosphoric or perchloric acid.

15. A process according to claim 1, wherein the inorganic acid is hydrochloric or sulfuric acid.

16. A process according to claim 1, wherein the concentration of the inorganic acid in the aqueous region of the reaction system is not less than 0.5 mole/kg and the total concentration of the inorganic acid radicals from the acid and the inorganic acid salt is 3.0-9.0 moles/kg.

17. A process according to claim 16, wherein the concentration of the inorganic acid is not less than 1.0 mole/kg and the total concentration of the inorganic acid radicals from the acid and the inorganic acid salt is 5.0-8.0 moles/kg.

18. A process according to claim 1, where the compound of general formula (I) is 2-methylbutene-1; 2-methylbutene-2; 3-methylbutene-1; an adduct of 2-methylbutene-1, 2-methylbutene-2, or 3-methylbutene-1 with sulfuric, phosphoric or perchloric acid; 2-methyl-2-chlorobutane; 2-methyl-2-bromobutane; 2-methyl-3-chlorobutane; 2-methyl-3-bromobutane; 2-methylbutan-2-ol or 3-methylbutan-2-ol.

19. A process according to claim 1, wherein 0.1-1-5 moles of formaldehyde is used per mole of the compound of general formula (I).

20. A process according to claim 19, wherein 0.8-1.1 moles of formaldehyde is used per mole of the compound of general formula (I).

21. A process according to claim 1, wherein the reaction temperature is 40°-200° C.

22. A process according to claim 21, wherein the reaction temperature is 70°-150° C.

23. A process according to claim 1, wherein the reaction pressure is atmospheric pressure to 30 kg/cm²(gauge).

24. A process for producing pinacolone from a compound of the general formula (II)

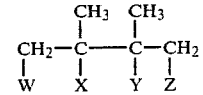

wherein either both W and Y are hydrogen atoms and X and Z are the same or different and each represents OH, Cl, Br, $HSO_4$, $H_2PO_4$, $ClO_4$ or RCOO in which R is a hydrogen atom or an alkyl group of 1 to 3 carbon atoms, or one of W and Y is a hydrogen atom and the other forms a single bond together with X, and Z represents OH, Cl, Br, $HSO_4$, $H_2PO_4$, $ClO_4$ or RCOO, comprising heating said compound of the general formula (II) in an aqueous solution of an inorganic acid selected from the group consisting of hydrochloric acid, hydrobromic acid, sulfuric acid, phosphoric acid and perchloric acid.

25. A process according to claim 24 wherein a salt of one or more of said inorganic acids, having a solubility of at least 35 grams per hundred grams of water at 100° C., is added to the reaction system.

26. The process of claim 25, wherein the salt is an alkali or alkaline earth metal salt of hydrochloric or sulfuric acid.

27. The process of claim 26, wherein the salt is sodium chloride, potassium chloride, lithium chloride, calcium chloride, magnesium chloride, sodium hydrogen sulfate, potassium hydrogen sulfate, lithium hydrogen sulfate or magnesium sulfate.

28. The process of claim 25, wherein said inorganic acid is hydrochloric, sulfuric, phosphoric or perchloric acid.

29. The process of claim 28, wherein the inorganic acid is hydrochloric or sulfuric acid.

30. The process of claim 25, wherein the concentration of the inorganic acid in the aqueous region of the reaction system is not less than 0.5 mole/kg, and the total concentration of the inorganic acid radicals from the acid and the inorganic acid salt is 3.0–9.0 moles/kg.

31. The process of claim 30, wherein the concentration of the inorganic acid is not less than 1.0 mole/kg and the total concentration of the inorganic acid radicals from the acid and the inorganic acid salt is 5.0–8.0 moles/kg.

32. The process of claim 25, wherein the reaction temperature is 40°–200° C.

33. The process of claim 32, wherein the reaction temperature is 70°–150° C.

34. The process of claim 25, wherein the reaction pressure is atmospheric pressure to 30 kg/cm$^2$ (gauge).

35. The process of claim 25, wherein the compound of general formula (II) is an alcohol selected from the group consisting of 2,3-dimethyl-butan-1,3-diol, 2,3-dimethyl-3-chlorobutan-1-ol, 2,3-dimethyl-3-bromobutan-1-ol, 2,3-dimethyl-3-buten-1-ol, 2,3-dimethyl-2-buten-1-ol and mixtures thereof, and esters of said alcohols with sulfuric, phosphoric or perchloric acid or with an aliphatic carboxylic acid containing 1–4 carbon atoms.

36. A process according to claim 1, wherein the salt is selected from the group consisting of (A) chlorides and bromides of lithium, sodium, potassium, rubidium, cesium, copper, (II), magnesium, calcium, strontium, barium, zinc, cadmium, aluminum, scandium, zirconium, titanium (IV), tin (IV), manganese (II), iron, cobalt (II), and nickel; (B) sulfates of ammonium, sodium, rubidium, cesium, magnesium, cadmium, zinc, aluminum, cobalt (II), copper (II), nickel (II) and manganese (II); (C) perchlorates of lithium, calcium, silver, strontium, sodium, barium and magnesium; (D) the hydrogen sulfates or the dihydrogen phosphates of sodium, potassium, lithium and ammonium; (and E) magnesium potassium chloride sulfate.

37. The process of claim 25 in which the salt is selected from the group consisting of (A) chlorides and bromides of lithium, sodium, potassium, rubidium, cesium, copper (II), magnesium, calcium, strontium, barium, zinc, cadmium, aluminum, scandium, zirconium, titanium (IV), tin (IV), manganese (II), iron, cobalt (II) and nickel; (B) sulfates of ammonium, sodium, rubidium, cesium, magnesium, cadmium, zinc, aluminum, cobalt (II), copper (II), nickel (II) and manganese (II); (C) perchlorates of lithium, calcium, silver, strontium, sodium, barium and magnesium; (D) the hydrogen sulfates or the dihydrogen phosphates of sodium, potassium, lithium and ammonium; and (E) magnesium potassium chloride sulfate.

* * * * *

UNITED STATES PATENT AND TRADEMARK OFFICE
CERTIFICATE OF CORRECTION

PATENT NO. : 4,224,252
DATED : September 23, 1980
INVENTOR(S) : Sanao Kyo et al.

It is certified that error appears in the above—identified patent and that said Letters Patent is hereby corrected as shown below:

On the Title Page insert:

-- (30) Foreign Application Priority Data

| May 15, 1978 (JP) | Japan.......53-57882 |
| June 15, 1978 (JP) | Japan.......53-73539 |
| August 21, 1978 (JP) | Japan.......53-101985 --. |

Cancel Clsim 14.

Claim 19, line 1, "0.1-1-5" should read -- 0.1-1.5 --.

On the Title Page after the Abstract, "37 Claims" should read -- 36 Claims --.

Signed and Sealed this

Third Day of February 1981

[SEAL]

Attest:

RENE D. TEGTMEYER

Attesting Officer          Acting Commissioner of Patents and Trademarks